United States Patent
Perrey et al.

(10) Patent No.: US 12,036,071 B2
(45) Date of Patent: Jul. 16, 2024

(54) METHOD AND SYSTEM FOR AUTOMATICALLY SETTING AN ELEVATIONAL TILT ANGLE OF A MECHANICALLY WOBBLING ULTRASOUND PROBE

(71) Applicant: GE Precision Healthcare LLC, Wauwatosa, WI (US)

(72) Inventors: Christian Perrey, Mondsee (AT); Martin Swoboda, Hohenzell (AT)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

(21) Appl. No.: 17/566,050

(22) Filed: Dec. 30, 2021

(65) Prior Publication Data
US 2023/0210498 A1 Jul. 6, 2023

(51) Int. Cl.
*A61B 8/00* (2006.01)
*A61B 8/08* (2006.01)

(52) U.S. Cl.
CPC .......... *A61B 8/4461* (2013.01); *A61B 8/0833* (2013.01); *A61B 8/463* (2013.01); *A61B 8/467* (2013.01)

(58) Field of Classification Search
CPC ..... A61B 8/4461; A61B 8/0833; A61B 8/463; A61B 8/467
See application file for complete search history.

(56) References Cited

U.S. PATENT DOCUMENTS

| | | | |
|---|---|---|---|
| 2009/0187104 A1* | 7/2009 | Yamagata | G01S 7/52085 600/443 |
| 2012/0157831 A1* | 6/2012 | Waki | A61B 8/4461 600/438 |
| 2016/0242740 A1* | 8/2016 | Day | A61B 8/14 |
| 2020/0178934 A1* | 6/2020 | Perrey | A61B 8/4254 |

* cited by examiner

*Primary Examiner* — Ashley K Buran
*Assistant Examiner* — Kaitlyn E Sebastian
(74) *Attorney, Agent, or Firm* — McAndrews, Held & Malloy, Ltd.; Daniel Bissing; David Bates

(57) ABSTRACT

A system and method for automatically setting an elevational tilt angle of a mechanically wobbling ultrasound probe is provided. The method includes acquiring, by a mechanically wobbling ultrasound probe of an ultrasound system, an ultrasound volume of a region of interest. The method includes analyzing, by at least one processor of the ultrasound system, the ultrasound volume to identify an ultrasound image slice depicting an anatomical object of interest. The ultrasound image slice corresponds with an elevational tilt angle. The method includes setting, by the at least one processor, the mechanically wobbling ultrasound probe to the elevational tilt angle corresponding with the ultrasound image slice depicting the anatomical object of interest. The method includes acquiring, by the mechanically wobbling ultrasound probe, a two-dimensional (2D) ultrasound image at the elevational tilt angle. The method includes causing, by the at least one processor, a display system to present the 2D ultrasound image.

20 Claims, 3 Drawing Sheets

# METHOD AND SYSTEM FOR AUTOMATICALLY SETTING AN ELEVATIONAL TILT ANGLE OF A MECHANICALLY WOBBLING ULTRASOUND PROBE

FIELD

Certain embodiments relate to ultrasound imaging. More specifically, certain embodiments relate to a method and system for automatically setting an elevational tilt angle of a mechanically wobbling ultrasound probe by analyzing an acquired ultrasound volume of a region of interest to identify an ultrasound image slice depicting an anatomical object of interest, the ultrasound image slice corresponding with an elevational tilt angle.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

When performing a two-dimensional (2D) ultrasound scan using a volumetric ultrasound probe, such as a mechanically wobbling ultrasound probe, the acquired scan plane is typically at a central position (i.e., the elevational tilt angle is at zero (0) degrees). Some ultrasound systems allow an ultrasound operator to manually change the elevational tilt angle of the acquired scan plane without moving the volumetric ultrasound probe by manipulating a knob, slider, or other suitable user input device. In this case, the ultrasound system continues to scan in 2D, but with the scan plane tilted in the elevation direction according to the user input. This feature may be useful when scanning certain anatomical structures, such as a left and right ovary via a volume endocavity probe. However, the manual adjustment of the elevational tilt angle via a user input device may be difficult to use, time consuming, and/or less experienced users may be unable to locate a target plane.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically setting an elevational tilt angle of a mechanically wobbling ultrasound probe, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
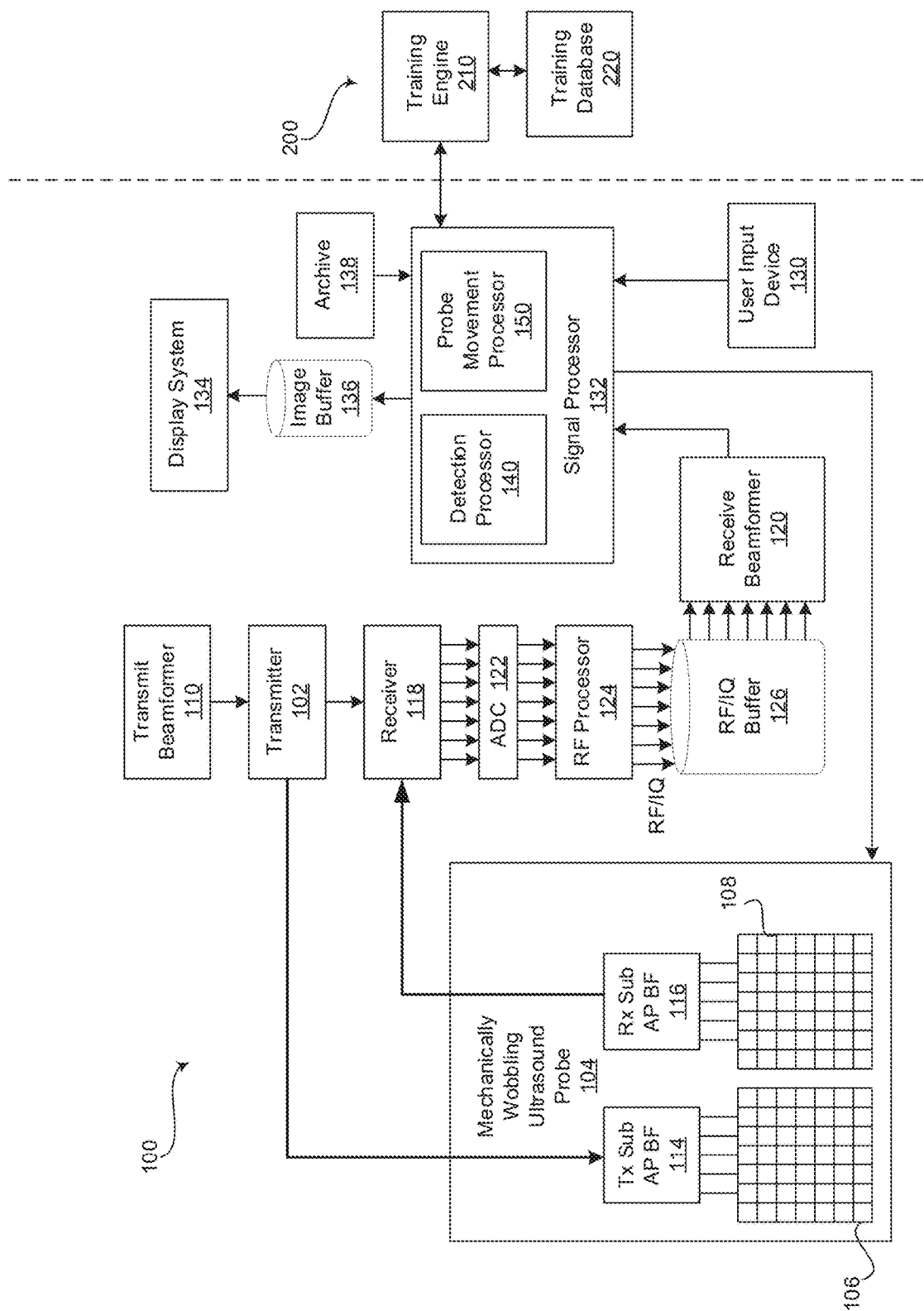
FIG. 1 is a block diagram of an exemplary ultrasound system that is operable to automatically set an elevational tilt angle of a mechanically wobbling ultrasound probe, in accordance with various embodiments.

Certain embodiments may be found in a method and system for automatically setting an elevational tilt angle of a mechanically wobbling ultrasound probe. Aspects of the present disclosure have the technical effect of automatically identifying an ultrasound image slice depicting an anatomical object of interest in an acquired ultrasound volume. Various embodiments have the technical effect of automatically setting an elevational tilt angle of a mechanically wobbling ultrasound probe to acquire two-dimensional (2D) ultrasound images in response to an identification of an ultrasound image slice depicting an anatomical object of interest in an acquired ultrasound volume. Certain embodiments have the technical effect of automatically analyzing 2D ultrasound images to determine whether to adjust an elevational tilt angle of a mechanically wobbling ultrasound probe.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as Brightness mode (B-mode or 2D mode), Motion mode (M-mode), three-dimensional (3D) mode, Color Flow mode (CF-mode), Pulsed Wave (PW) Doppler, Continuous Wave (CW) Doppler, Contrast Enhanced Ultrasound (CEUS), and/or sub-modes of B-mode and/or CF such as Harmonic Imaging, Shear Wave Elasticity Imaging (SWEI), Strain Elastography, Tissue Velocity Imaging (TVI), Power Doppler Imaging (PDI), B-flow, Micro Vascular Imaging (MVI), Ultrasound-Guided Attenuation Parameter (UGAP), and in some cases also Motion Mode (MM), Color Motion (CM), Tissue Velocity Doppler (TVD) where the "image" and/or "plane" includes a single beam or multiple beams.

Furthermore, the term processor or processing unit, as used herein, refers to any type of processing unit that can carry out the required calculations needed for the various embodiments, such as single or multi-core: Central Processing Unit (CPU), Accelerated Processing Unit (APU), Graphic Processing Unit (GPU), Digital Signal Processor (DSP), Field Programmable Gate Array (FPGA), Application-Specific Integrated Circuit (ASIC) or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to automatically set an elevational tilt angle 304 of a mechanically wobbling ultrasound probe 104, in accordance with various embodiments. Referring to FIG. 1, there is shown an ultrasound system 100 and a training system 200. The ultrasound system 100 comprises a transmitter 102, a mechanically wobbling ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive a mechanically wobbling ultrasound probe 104. The mechanically wobbling ultrasound probe 104 may comprise a one dimensional (1D) array of piezoelectric elements mounted on a transducer assembly movable in a single plane. For example, the transducer assembly may be movable approximately 120 to 150 degrees by a motor driving gears, belts, and/or rope to pivot an axis or hub of the transducer assembly. The mechanically wobbling ultrasound probe 104 may comprise a group of transmit transducer elements 106 and a group of receive transducer elements 108, that normally constitute the same elements mounted on the mechanical transducer assembly. The mechanical transducer assembly may be disposed in oil within a probe body having a probe cap. The group of transmit transducer elements 106 may emit ultrasonic signals through the oil and probe cap and into a target. In certain embodiment, the mechanically wobbling ultrasound probe 104 may be operable to acquire ultrasound image data covering at least a substantial portion of an anatomy, such as an ovary, a fetus, a heart, a blood vessel, or any suitable anatomical structure. The mechanically wobbling ultrasound probe 104 may be operated in a 2D ultrasound acquisition mode and/or a volume acquisition mode. In a volume acquisition mode, the transducer assembly of the mechanically wobbling ultrasound probe 104 is moved to acquire a plurality of 2D ultrasound images at a plurality of different elevational tilt angles, the plurality of 2D ultrasound images forming an ultrasound volume. In a 2D ultrasound acquisition mode, the mechanically wobbling ultrasound probe 104 acquires 2D ultrasound images at a particular elevational tilt angle.

Figure 2:
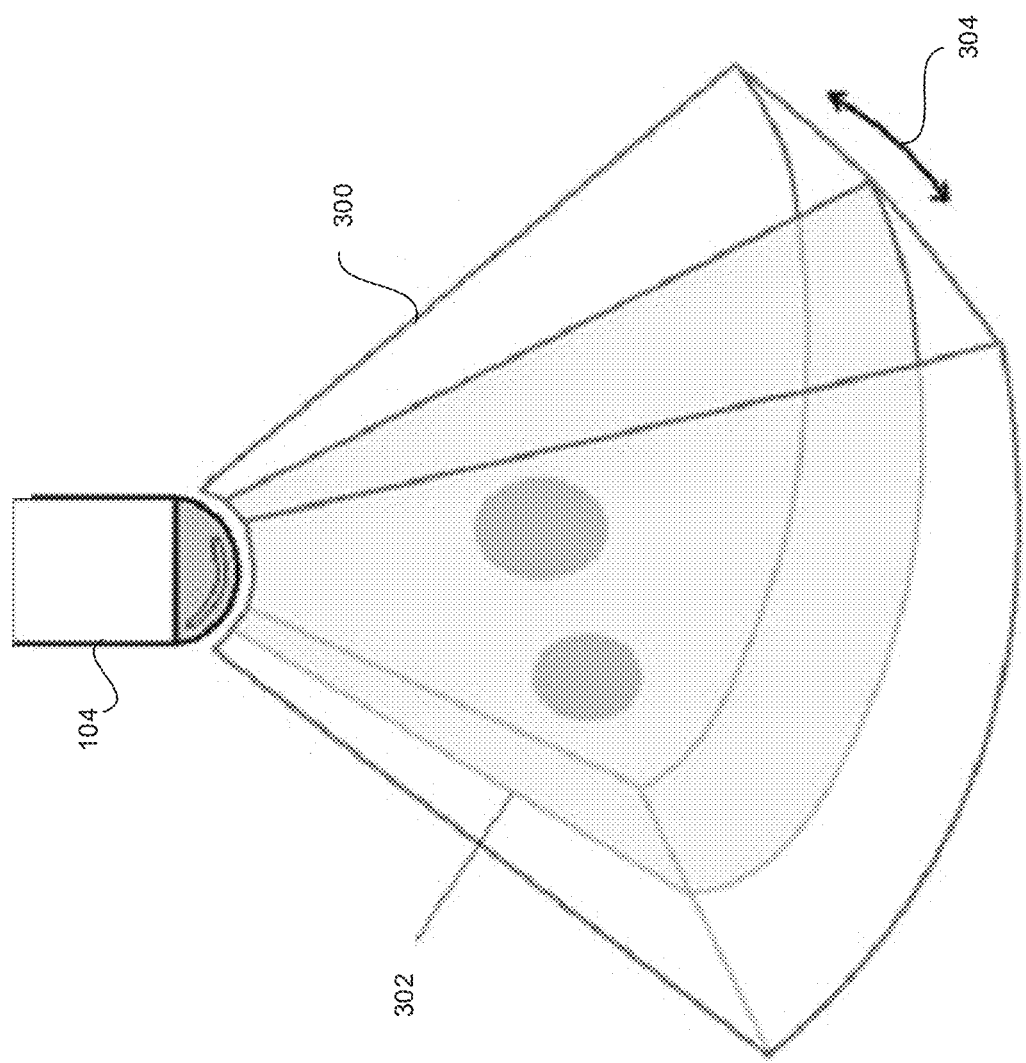
FIG. 2 is a perspective view of an exemplary mechanically wobbling ultrasound probe acquiring a two-dimensional (2D) ultrasound image within an ultrasound volume, the 2D ultrasound image acquired at an angle tilted in an elevational direction, in accordance with various embodiments.

FIG. 2 is a perspective view of an exemplary mechanically wobbling ultrasound probe 104 acquiring a two-dimensional (2D) ultrasound image 302 within an ultrasound volume 300, the 2D ultrasound image 302 acquired at an angle tilted in an elevational direction 304, in accordance with various embodiments. Referring to FIG. 2, the mechanically wobbling ultrasound probe 104 may acquire a 2D ultrasound image 302 at a particular elevational tilt angle 304. Additionally and/or alternatively, the mechanically wobbling ultrasound probe 104 may acquire an ultrasound volume 300 formed by a plurality of 2D ultrasound images 302 acquired at a plurality of different elevational tilt angles 304.

Referring again to FIG. 1, the transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the mechanically wobbling ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that is representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select an ultrasound view, select an anatomical object of interest, select and/or adjust an elevational tilt angle, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the mechanically wobbling ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the mechanically wobbling ultrasound probe 104, for example. As an example, user input device 130 may include a touchscreen display.

As another example, the mechanically wobbling ultrasound probe 104 may include a mouse wheel, touch pad, or the like to provide manual elevational tilt angle adjustments to an elevational tilt angle automatically selected by the signal processor 132. In various embodiments, the manual elevational tilt angle adjustments are fine angular adjustments (i.e., 0.5-1.5 degree adjustments). As an example, if the ultrasound system 100 automatically presents a 2D ultrasound image of an anatomical object of interest, an ultrasound operator may manually provide fine angular adjustments via the user input device 130. The user input device 130 may include buttons or sliders on a touchscreen display, a rotary encoder on a control panel, a touch pad on the mechanically wobbling ultrasound probe 104, a mouse wheel on the mechanically wobbling ultrasound probe 104, and/or any suitable user input device 130. In a representative embodiment, the user input device 130 may include buttons or the like for instructing the ultrasound system 100 to perform a volume rescan when acquired 2D ultrasound images do not accurately depict the anatomical object of interest.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a detection processor 140 and a probe movement processor 150. The signal processor 132 may be capable of receiving input information from a user input device 130 and/or archive 138, generating an output displayable by a display system 134, and manipulating the output in response to input information from a user input device 130, among other things. The signal processor 132, detection processor 140, and probe movement processor 150 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a detection processor 140 that comprises suitable logic, circuitry, interfaces and/or code that may be operable to analyze an acquired ultrasound volume 300 to identify an ultrasound image slice 302 depicting an anatomical object of interest (i.e., a desired anatomical structure or a desired view of an anatomical structure). For example, the anatomical object of interest may be a particular anatomical structure, such as an ovary follicle, a left ovary, a right ovary, a fetus, a heart, and or any suitable anatomical structure. As another example, the anatomical object of interest may be a particular view of an anatomical structure, such as a four chamber (4CH) or two chamber (2CH) view of a heart, or any suitable view of any suitable anatomical structure. The detection processor 140 may be configured to receive a selection of the anatomical object of interest. For example, the detection processor 140 may receive a selection of a 4CH view of a heart from an ultrasound operator via the user input device 130 at an onset of an ultrasound examination. Additionally and/or alternatively, the detection processor 140 may be configured to automatically determine the anatomical object of interest. For example, the detection processor 140 may be configured to analyze an acquired ultrasound volume 300 and determine, based on the analysis, that the anatomical object of interest is an ovary follicle. The ultrasound image slice 302 depicting the anatomical object of interest and identified by the detection processor corresponds with an elevational tilt angle 304. For example, the ultrasound slice 302 depicting the anatomical object of interest is a 2D ultrasound image 302 acquired at a particular elevational tilt angle 304 as part of the acquisition of the ultrasound volume 300. The detection processor 140 may include image analysis algorithms, artificial intelligence algorithms, one or more deep neural networks (e.g., a convolutional neural network) and/or may utilize any suitable form of image analysis techniques or machine learning processing functionality configured to identify an ultrasound image slice 302 depicting an anatomical object of interest in the ultrasound volume 300. The detection processor 140 may present the identified ultrasound image slice 302 at the display system 134 and/or store the identified ultrasound image slice 302 at archive 138 and/or any suitable data storage medium.

The detection processor 140 may comprise suitable logic, circuitry, interfaces and/or code that may be operable to automatically identify an ultrasound image slice 302 depicting an anatomical object of interest in an acquired ultrasound volume 300. In various embodiments, the detection processor 140 may be provided as a deep neural network that may be made up of, for example, an input layer, an output layer, and one or more hidden layers in between the input and output layers. Each of the layers may be made up of a plurality of processing nodes that may be referred to as neurons. For example, the detection processor 140 may include an input layer having a neuron for each pixel or a group of pixels from an ultrasound volume 300 of a region of interest. The output layer may have neurons corresponding to an ultrasound slice 302 depicting the anatomical object of interest. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the detection processor 140 deep neural network (e.g., convolutional neural network) may identify an ultrasound image slice 302 depicting an anatomical object of interest in an acquired ultrasound volume 300 with a high degree of probability.

The detection processor 140 may be configured to provide the elevational tilt angle 304 of the identified ultrasound image slice 302 to the probe movement processor 150. As described in more detail below, the probe movement processor 150 may be configured to automatically set the mechanically wobbling ultrasound probe 104 to the elevational tilt angle 304 corresponding with the ultrasound image slice 302 depicting the anatomical object of interest. The mechanically wobbling ultrasound probe 104 is configured to acquire 2D ultrasound images at the elevational tilt angle 304 set by the probe movement processor 150. In various embodiments, the detection processor 140 may comprise suitable logic, circuitry, interfaces and/or code that may be operable to automatically analyze the acquired 2D ultrasound images to determine whether the acquired 2D ultrasound images continue to accurately depict the anatomical object of interest. For example, if an ultrasound operator inadvertently moves the mechanically wobbling ultrasound probe 104 or the anatomical object of interest moves (e.g., a fetus), the elevational tilt angle at which the mechanically wobbling ultrasound probe 104 is set may no longer provide 2D ultrasound images of the anatomical object of interest. The detection processor 140 may be configured to analyze the 2D ultrasound images in view of the ultrasound slice 302 identified in the ultrasound volume 300 to determine whether the 2D ultrasound images provides the desired view of the anatomical object of interest. In an exemplary embodiment, if the 2D ultrasound images no longer provide an accurate depiction of the anatomical object of interest, the detection processor 140 may be configured to instruct the mechanically wobbling ultrasound probe 104 to acquire a new ultrasound volume 300 of the region of interest, which the detection processor 140 analyzes to identify a new ultrasound image slice 302 depicting the anatomical object of interest. In a representative embodiment, the detection processor 140 may be configured to instruct the mechanically wobbling ultrasound probe 104 to acquire the new ultrasound volume 300 of only a portion of the region of interest for analysis by the detection processor 140. For example, the detection processor 140 may apply image quality threshold(s) to determine an amount of movement from the desired view of the anatomical object of interest. As an example, a small amount of movement that does not noticeably affect an image quality may result in no volume rescan, a medium amount of movement affecting the image quality of the anatomical object of interest may result in rescanning a portion of the region of interest in the vicinity of the current elevational tilt angle, and a large amount of movement where the anatomical object of interest is no longer visible in the 2D ultrasound images may result in a full rescan of the region of interest. The detection processor 140 may be configured to apply image quality thresholds to determine whether a full volume rescan, partial volume rescan, or no volume rescan is performed. In various embodiments, the detection processor 140 may be configured to automatically analyze only every nth acquired 2D ultrasound image. For example, the detection processor 140 may be configured to analyze every 5th, 10th, 20th, or any suitable number of acquired 2D ultrasound images to determine whether the anatomical object of interest is accurately depicted.

The detection processor 140 may comprise suitable logic, circuitry, interfaces and/or code that may be operable to automatically analyze acquired 2D ultrasound images to determine whether the acquired 2D ultrasound images continue to accurately depict the anatomical object of interest. The detection processor 140 may include image analysis algorithms, artificial intelligence algorithms, one or more deep neural networks (e.g., a convolutional neural network) and/or may utilize any suitable form of image analysis techniques or machine learning processing functionality configured to classify an amount of movement between a 2D ultrasound image and a previously identified ultrasound slice 302 depicting an anatomical object of interest. In various embodiments, the detection processor 140 may be provided as a deep neural network that may be made up of, for example, an input layer, an output layer, and one or more hidden layers in between the input and output layers. Each of the layers may be made up of a plurality of processing nodes that may be referred to as neurons. For example, the detection processor 140 may include an input layer having a neuron for each pixel or a group of pixels from a 2D ultrasound image. The output layer may have neurons corresponding to an amount of movement between the 2D ultrasound image and a previously identified ultrasound slice 302 depicting the anatomical object of interest. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the detection processor 140 deep neural network (e.g., convolutional neural network) may classify an amount of movement between the 2D ultrasound image and a previously identified ultrasound slice 302 depicting the anatomical object of interest with a high degree of probability.

The signal processor 132 may include a probe movement processor 150 that comprises suitable logic, circuitry, interfaces and/or code that may be operable to automatically set the mechanically wobbling ultrasound probe 104 to the elevational tilt angle 304 corresponding with the ultrasound image slice 302 depicting the anatomical object of interest. For example, the probe movement processor 150 may be configured to receive an elevational tilt angle 304 from the detection processor 140. The probe movement processor 150 may instruct the mechanically wobbling ultrasound probe 104 to move the transducer assembly having the one dimensional (1D) array of piezoelectric elements to the selected elevational tilt angle 304. The mechanically wobbling ultrasound probe 104 may move the transducer assembly to the set elevational tilt angle 304 and acquire 2D ultrasound images at the elevational tilt angle 304 set by the probe movement processor 150. In various embodiments, the probe movement processor 150 may be configured to receive a manual elevational tilt angle adjustment that is a fine angular adjustment (i.e., 0.5-1.5 degree adjustments) via a user input device 130. As an example, if the ultrasound system 100 presents a 2D ultrasound image of an anatomical object of interest at the display system 134, an ultrasound operator may manually provide the fine angular adjustment via the user input device 130 to the probe movement processor 150. The probe movement processor 150 may be configured to adjust the elevational tilt angle 304 of the mechanically wobbling ultrasound probe 104 based on the fine angular adjustment.

The display system 134 may be any device capable of communicating visual information to a user. For example, a display system 134 may include a liquid crystal display, a light emitting diode display, and/or any suitable display or displays. The display system 134 can be operable to present the ultrasound image slice 302 identified as having the anatomical object of interest, 2D ultrasound images acquired at the set elevational tilt angle 304, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound volumes 300, ultrasound image slices 302, instructions for identifying an ultrasound image slice 302 depicting the anatomical object of interest, instructions for automatically moving an elevational tilt angle of a mechanically wobbling ultrasound probe 104, instructions for analyzing 2D ultrasound images acquired by the mechanically wobbling ultrasound probe 104 at the selected elevational tilt angle 304, and/or instructions for providing full and/or partial rescan commands, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 160 may comprise suitable logic, circuitry, interfaces and/or code that may be operable to train the neurons of the deep neural network(s) (e.g., artificial intelligence model(s)) inferenced (i.e., deployed) by the detection processor 140. For example, the artificial intelligence model inferenced by the detection processor 140 may be trained to automatically identify an ultrasound image slice 302 depicting an anatomical object of interest in an acquired ultrasound volume 300 using database(s) 220 of classified ultrasound volumes of anatomical objects of interest. As an example, the training engine 210 may train the deep neural networks deployed by the detection processor 140 to automatically classify an amount of movement between the 2D ultrasound image and a previously identified ultrasound slice 302 depicting the anatomical object of interest using database(s) 220 of classified 2D ultrasound images.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 3:
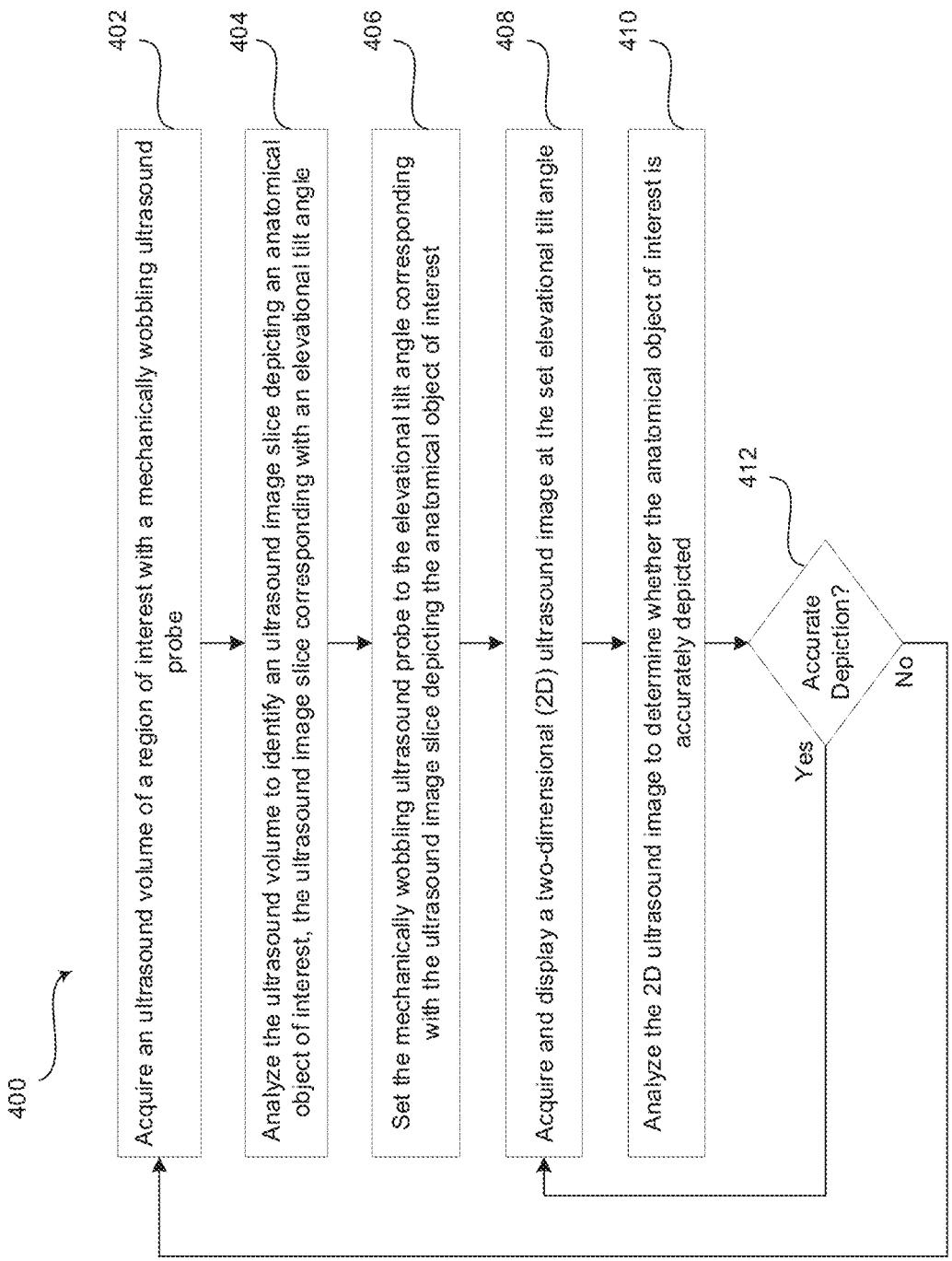
FIG. 3 is a flow chart illustrating exemplary steps that may be utilized for automatically setting an elevational tilt angle of a mechanically wobbling ultrasound probe, in accordance with various embodiments.

FIG. 3 is a flow chart 400 illustrating exemplary steps 402-412 that may be utilized for automatically setting an elevational tilt angle 304 of a mechanically wobbling ultrasound probe 104, in accordance with various embodiments. Referring to FIG. 3, there is shown a flow chart 400 comprising exemplary steps 402 through 412. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a mechanically wobbling ultrasound probe 104 of an ultrasound system 100 acquires an ultrasound volume 300 of a region of interest. For example, the mechanically wobbling ultrasound probe 104 may comprise a one dimensional (1D) array of piezoelectric elements mounted on a transducer assembly movable in a single plane. The mechanically wobbling ultrasound probe 104 may be operated in a volume acquisition mode, where the transducer assembly of the mechanically wobbling ultrasound probe 104 is automatically moved to acquire a plurality of ultrasound image slices 302 at a plurality of different elevational tilt angles 304, and where the plurality of ultrasound image slices 302 form the ultrasound volume 300.

At step 404, a signal processor 132 of the ultrasound system 100 may analyze the ultrasound volume 300 to identify an ultrasound image slice 302 depicting an anatomical object of interest, the ultrasound image slice 302 corresponding with an elevational tilt angle 304. For example, a detection processor 140 of the signal processor 132 may be configured to receive a selection of the anatomical object of interest and/or may be configured to automatically determine the anatomical object of interest. The ultrasound image slice 302 depicting the anatomical object of interest and identified by the detection processor corresponds with an elevational tilt angle 304. For example, the ultrasound slice 302 depicting the anatomical object of interest is a 2D ultrasound image 302 acquired at a particular elevational tilt angle 304 as part of the acquisition of the ultrasound volume 300 at step 402. The detection processor 140 may include image analysis algorithms, artificial intelligence algorithms, one or more deep neural networks (e.g., a convolutional neural network) and/or may utilize any suitable form of image analysis techniques or machine learning processing functionality configured to identify an ultrasound image slice 302 depicting an anatomical object of interest in the ultrasound volume 300. The detection processor 140 may be configured to provide the elevational tilt angle 304 of the identified ultrasound image slice 302 to the probe movement processor 150.

At step 406, the signal processor 132 of the ultrasound system 100 may set the mechanically wobbling ultrasound probe 104 to the elevational tilt angle 304 corresponding with the ultrasound image slice 302 depicting the anatomical object of interest. For example, a probe movement processor 150 of the signal processor 132 may be configured to receive an elevational tilt angle 304 from the detection processor 140. The probe movement processor 150 may instruct the mechanically wobbling ultrasound probe 104 to move the transducer assembly having the one dimensional (1D) array of piezoelectric elements to the selected elevational tilt angle 304. The mechanically wobbling ultrasound probe 104 may move the transducer assembly to the set elevational tilt angle 304 as instructed by the probe movement processor 150.

At step 408, the ultrasound system 100 may acquire and present a two-dimensional (2D) ultrasound image at the set elevational tilt angle 304. For example, the mechanically wobbling ultrasound probe 104, set to the elevational tilt angle 304 at step 406, acquires 2D ultrasound images for presentation at the display system 134. In various embodiments, the probe movement processor 150 of the signal processor 132 may be configured to receive a manual elevational tilt angle adjustment that is a fine angular adjustment (i.e., 0.5-1.5 degree adjustments) via a user input device 130. As an example, if the ultrasound system 100 presents a 2D ultrasound image of an anatomical object of interest at the display system 134, an ultrasound operator may manually provide the fine angular adjustment via the user input device 130 to the probe movement processor 150. In this case, the process 400 returns to step 406 to set the mechanically wobbling ultrasound probe 104 based on the fine angular adjustment to the elevational tilt angle 304.

At step 410, the signal processor 132 of the ultrasound system 100 may analyze the 2D ultrasound image to determine whether the anatomical object of interest is accurately depicted. For example, the detection processor 140 of the signal processor 132 may be configured to automatically analyze the acquired 2D ultrasound images to determine whether the acquired 2D ultrasound images continue to accurately depict the anatomical object of interest. As an example, if an ultrasound operator inadvertently moves the mechanically wobbling ultrasound probe 104 or the anatomical object of interest moves (e.g., a fetus), the elevational tilt angle at which the mechanically wobbling ultrasound probe 104 is set may no longer provide 2D ultrasound images of the anatomical object of interest. The detection processor 140 may be configured to analyze the 2D ultrasound images in view of the ultrasound slice 302 identified in the ultrasound volume 300 to determine whether the 2D ultrasound images provides the desired view of the anatomical object of interest. The detection processor 140 may include image analysis algorithms, artificial intelligence algorithms, one or more deep neural networks (e.g., a convolutional neural network) and/or may utilize any suitable form of image analysis techniques or machine learning processing functionality configured to classify an amount of movement between a 2D ultrasound image and a previously identified ultrasound slice 302 depicting an anatomical object of interest. In various embodiments, the detection processor 140 may be configured to automatically analyze only every nth acquired 2D ultrasound image. For example, the detection processor 140 may be configured to analyze every 5th, 10th, 20th, or any suitable number of acquired 2D ultrasound images to determine whether the anatomical object of interest is accurately depicted.

At step 412, if the amount of movement is less than an image quality threshold, the anatomical object of interest is accurately depicted and the process 400 returns to step 408 to continue acquiring and displaying 2D ultrasound images at the set elevational tilt angle. If the amount of movement exceeds the image quality threshold, the process returns to step 402 to perform a volume rescan. In an exemplary embodiment, if the 2D ultrasound images no longer provide an accurate depiction of the anatomical object of interest, the detection processor 140 may be configured to instruct the mechanically wobbling ultrasound probe 104 to either acquire a full new ultrasound volume 300 of the region of interest or a partial ultrasound volume in a vicinity of the set elevational tilt angle 304. For example, the detection processor 140 may apply image quality threshold(s) to the amount of movement from the desired view of the anatomical object of interest determined at step 410. In certain embodiments, a small amount of movement that does not noticeably affect an image quality may result in no volume rescan, a medium amount of movement affecting the image quality of the anatomical object of interest may result in rescanning a portion of the region of interest in the vicinity of the current elevational tilt angle, and a large amount of movement where the anatomical object of interest is no longer visible in the 2D ultrasound images may result in a full rescan of the region of interest. The detection processor 140 may be configured to apply image quality thresholds to determine whether a full volume rescan is performed at step 402, a partial volume rescan is performed at step 402, or no volume rescan is performed and the processor 400 returns to step 408. The process 400 may continue until the ultrasound examination has been completed.

Aspects of the present disclosure provide a method 400 and system 100 for automatically setting an elevational tilt angle 304 of a mechanically wobbling ultrasound probe 104. In accordance with various embodiments, the method 400 may comprise acquiring 402, by a mechanically wobbling ultrasound probe 104 of an ultrasound system 100, an ultrasound volume 300 of a region of interest. The method 400 may comprise analyzing 404, by at least one processor 132, 140 of the ultrasound system 100, the ultrasound volume 300 to identify an ultrasound image slice 302 depicting an anatomical object of interest. The ultrasound image slice 302 corresponds with an elevational tilt angle 304. The method 400 may comprise setting 406, by the at least one processor 132, 150, the mechanically wobbling ultrasound probe 104 to the elevational tilt angle 304 corresponding with the ultrasound image slice 302 depicting the anatomical object of interest. The method 400 may comprise acquiring 408, by the mechanically wobbling ultrasound probe 104, a two-dimensional (2D) ultrasound image at the elevational tilt angle 304. The method 400 may comprise causing 408, by the at least one processor 132, a display system 134 to present the 2D ultrasound image.

In an exemplary embodiment, the method 400 may comprise analyzing 410, by the at least one processor 132, 140, the 2D ultrasound image to determine whether the anatomical object of interest is accurately depicted based on an amount of movement between the ultrasound image slice 302 and the 2D ultrasound image. In a representative embodiment, when the anatomical object of interest is accurately depicted in the 2D ultrasound image based on the amount of movement between the ultrasound image slice 302 and the 2D ultrasound image being below a first image quality threshold, the method 400 comprises acquiring 408, by the mechanically wobbling ultrasound probe 104, an additional 2D ultrasound image at the elevational tilt angle 304. The method 400 comprises causing 408, by the at least one processor 132, the display system 134 to present the additional 2D ultrasound image. In various embodiments, when the anatomical object of interest is not accurately depicted in the 2D ultrasound image based on the amount of movement between the ultrasound image slice 302 and the 2D ultrasound image being above a first image quality threshold and below a second image quality threshold, the method 400 comprises acquiring 402, by the mechanically wobbling ultrasound probe 104, an additional ultrasound volume 300 of a portion of the region of interest in a vicinity of the elevational tilt angle 304. The method 400 comprises analyzing 404, by the at least one processor 132, 140, the additional ultrasound volume 300 to identify a new ultrasound image slice 302 depicting the anatomical object of interest. The new ultrasound image slice 302 corresponds with a new elevational tilt angle 304. The method 400 comprises setting 406, by the at least one processor 132, 150, the mechanically wobbling ultrasound probe 104 to the new elevational tilt angle 304 corresponding with the new ultrasound image slice 302 depicting the anatomical object of interest. The method 400 comprises acquiring 408, by the mechanically wobbling ultrasound probe 104, an additional 2D ultrasound image at the new elevational tilt angle 304. The method 400 comprises causing 408, by the at least one processor 132, the display system 134 to present the additional 2D ultrasound image. In certain embodiments, when the anatomical object of interest is not accurately depicted in the 2D ultrasound image based on the amount of movement between the ultrasound image slice 302 and the 2D ultrasound image being above a first image quality threshold and above a second image quality threshold, the method 400 comprises acquiring 402, by the mechanically wobbling ultrasound probe 104, an additional ultrasound volume 300 of the region of interest in a vicinity of the elevational tilt angle 304. The method 400 comprises analyzing 404, by the at least one processor 132, 140, the additional ultrasound volume 300 to identify a new ultrasound image slice 302 depicting the anatomical object of interest. The new ultrasound image slice corresponds with a new elevational tilt angle 304. The method 400 comprises setting 406, by the at least one processor 132, 150, the mechanically wobbling ultrasound probe 104 to the new elevational tilt angle 304 corresponding with the new ultrasound image slice 302 depicting the anatomical object of interest. The method 400 comprises acquiring 408, by the mechanically wobbling ultrasound probe 104, an additional 2D ultrasound image at the new elevational tilt angle 304. The method 400 comprises causing 408, by the at least one processor 132, the display system 134 to present the additional 2D ultrasound image. In an exemplary embodiment, the anatomical object of interest is one or both of a particular anatomical structure, or a particular ultrasound image view of a particular anatomical structure. In a representative embodiment, the method 400 may comprise receiving 408, by the at least one processor 132, 150, a user input providing a fine angular adjustment to the elevational tilt angle 304. The method 400 may comprise setting 406, by the at least one processor 132, 150, the mechanically wobbling ultrasound probe 104 to an adjusted elevational tilt angle 304 based on the fine angular adjustment. The method 400 may comprise acquiring 408, by the mechanically wobbling ultrasound probe 104, an adjusted two-dimensional (2D) ultrasound image at the adjusted elevational tilt angle 304. The method 400 may comprise causing 408, by the at least one processor 132, the display system 134 to present the adjusted 2D ultrasound image.

Various embodiments provide a system 100 for automatically setting an elevational tilt angle of a mechanically wobbling ultrasound probe. The system 100 may comprise a mechanically wobbling ultrasound probe 104, at least one processor 132, 140, 150, and a display system 134. The mechanically wobbling ultrasound probe 104 may be configured to acquire an ultrasound volume 300 of a region of interest. The mechanically wobbling ultrasound probe 104 may be configured to acquire a two-dimensional (2D) ultrasound image at an elevational tilt angle 304. The at least one processor 132, 140 may be configured to analyze the ultrasound volume 300 to identify an ultrasound image slice 302 depicting an anatomical object of interest. The ultrasound image slice 302 corresponds with the elevational tilt angle 304. The at least one processor 132, 150 may be configured to set the mechanically wobbling ultrasound probe 104 to the elevational tilt angle 304 corresponding with the ultrasound image slice 302 depicting the anatomical object of interest. The display system 134 may be configured to present the 2D ultrasound image.

In a representative embodiment, the at least one processor 132, 140 is configured to analyze the 2D ultrasound image to determine whether the anatomical object of interest is accurately depicted based on an amount of movement between the ultrasound image slice 302 and the 2D ultrasound image. In various embodiments, when the anatomical object of interest is accurately depicted in the 2D ultrasound image based on the amount of movement between the ultrasound image slice 302 and the 2D ultrasound image being below a first image quality threshold, the mechanically wobbling ultrasound probe 104 is configured to acquire an additional 2D ultrasound image at the elevational tilt angle 304. The display system 134 is configured to present the additional 2D ultrasound image. In certain embodiments, when the anatomical object of interest is not accurately depicted in the 2D ultrasound image based on the amount of movement between the ultrasound image slice 302 and the 2D ultrasound image being above a first image quality threshold and below a second image quality threshold, the mechanically wobbling ultrasound probe 104 is configured to acquire an additional ultrasound volume 300 of a portion of the region of interest in a vicinity of the elevational tilt angle 304. The at least one processor 132, 140 is configured to analyze the additional ultrasound volume 300 to identify a new ultrasound image slice 302 depicting the anatomical object of interest. The new ultrasound image slice 302 corresponds with a new elevational tilt angle 304. The at least one processor 132, 150 is configured to set the mechanically wobbling ultrasound probe 104 to the new elevational tilt angle 304 corresponding with the new ultrasound image slice 302 depicting the anatomical object of interest. The mechanically wobbling ultrasound probe 104 is configured to acquire an additional 2D ultrasound image at the new elevational tilt angle 304. The display system 134 is configured to present the additional 2D ultrasound image. In an exemplary embodiment, when the anatomical object of interest is not accurately depicted in the 2D ultrasound image based on the amount of movement between the ultrasound image slice 302 and the 2D ultrasound image being above a first image quality threshold and above a second image quality threshold, the mechanically wobbling ultrasound probe 104 is configured to acquire an additional ultrasound volume 300 of the region of interest. The at least one processor 132, 140 is configured to analyze the additional ultrasound volume 300 to identify a new ultrasound image slice 302 depicting the anatomical object of interest. The new ultrasound image slice 302 corresponds with a new elevational tilt angle 304. The at least one processor 132, 150 is configured to set the mechanically wobbling ultrasound probe 104 to the new elevational tilt angle 304 corresponding with the new ultrasound image slice 302 depicting the anatomical object of interest. The mechanically wobbling ultrasound probe 104 is configured to acquire an additional 2D ultrasound image at the new elevational tilt angle 304. The display system 134 is configured to present the additional 2D ultrasound image. In a representative embodiment, the at least one processor 132, 150 is configured to receive a user input providing a fine angular adjustment to the elevational tilt angle 304. The at least one processor 132, 150 is configured to set the mechanically wobbling ultrasound probe 104 to an adjusted elevational tilt angle 304 based on the fine angular adjustment. The mechanically wobbling ultrasound probe 104 is configured to acquire an adjusted two-dimensional (2D) ultrasound image at the adjusted elevational tilt angle 304. The display system 134 is configured to present the adjusted 2D ultrasound image. In various embodiments, the mechanically wobbling ultrasound probe 104 comprises a user input device 130 configured to provide the fine angular adjustment of the elevational tilt angle to the at least one processor 132, 150.

Certain embodiments provide a non-transitory computer readable medium having stored thereon, a computer program having at least one code section. The at least one code section is executable by a machine for causing an ultrasound system 100 to perform steps 400. The steps 400 may comprise receiving 402, from a mechanically wobbling ultrasound probe 104 of the ultrasound system 100, an ultrasound volume 300 of a region of interest. The steps 400 may comprise analyzing 404 the ultrasound volume 300 to identify an ultrasound image slice 302 depicting an anatomical object of interest. The ultrasound image slice 302 corresponds with an elevational tilt angle 304. The steps 400 may comprise setting 406 the mechanically wobbling ultrasound probe 104 to the elevational tilt angle 304 corresponding with the ultrasound image slice 302 depicting the anatomical object of interest. The steps 400 may comprise receiving 408, from the mechanically wobbling ultrasound probe 104, a two-dimensional (2D) ultrasound image at the elevational tilt angle 304. The steps 400 may comprise causing 408 a display system 134 to present the 2D ultrasound image.

In various embodiments, the steps 400 may comprise analyzing 410 the 2D ultrasound image to determine whether the anatomical object of interest is accurately depicted based on an amount of movement between the ultrasound image slice 302 and the 2D ultrasound image. In certain embodiments, when the anatomical object of interest is accurately depicted in the 2D ultrasound image based on the amount of movement between the ultrasound image slice and the 2D ultrasound image being below a first image quality threshold, the steps 400 may comprise receiving 408, from the mechanically wobbling ultrasound probe 104, an additional 2D ultrasound image at the elevational tilt angle 304. The steps 400 may comprise causing 408, by the at least one processor 132, the display system 134 to present the additional 2D ultrasound image. In an exemplary embodiment, when the anatomical object of interest is not accurately depicted in the 2D ultrasound image based on the amount of movement between the ultrasound image slice 302 and the 2D ultrasound image being above a first image quality threshold and below a second image quality threshold, the steps 400 may comprise receiving 402, from the mechanically wobbling ultrasound probe 104, an additional ultrasound volume 300 of a portion of the region of interest in a vicinity of the elevational tilt angle 304. The steps 400 may comprise analyzing 404 the additional ultrasound volume to identify a new ultrasound image slice 302 depicting the anatomical object of interest. The new ultrasound image slice 302 corresponds with a new elevational tilt angle 304. The steps 400 may comprise setting 406 the mechanically wobbling ultrasound probe 104 to the new elevational tilt angle 304 corresponding with the new ultrasound image slice 302 depicting the anatomical object of interest. The steps 400 may comprise receiving 408, from the mechanically wobbling ultrasound probe 104, an additional 2D ultrasound image at the new elevational tilt angle 304. The steps 400 may comprise causing 408 the display system 134 to present the additional 2D ultrasound image. In a representative embodiment, when the anatomical object of interest is not accurately depicted in the 2D ultrasound image based on the amount of movement between the ultrasound image slice 302 and the 2D ultrasound image being above a first image quality threshold and above a second image quality threshold, the steps 400 may comprise receiving 402, from the mechanically wobbling ultrasound probe 104, an additional ultrasound volume 300 of the region of interest. The steps 400 may comprise analyzing 404 the additional ultrasound volume to identify a new ultrasound image slice 302 depicting the anatomical object of interest. The new ultrasound image slice 302 corresponds with a new elevational tilt angle 304. The steps 400 may comprise setting 406 the mechanically wobbling ultrasound probe 104 to the new elevational tilt angle 304 corresponding with the new ultrasound image slice 302 depicting the anatomical object of interest. The steps 400 may comprise receiving 408, from the mechanically wobbling ultrasound probe 104, an additional 2D ultrasound image at the new elevational tilt angle 304. The steps 400 may comprise causing 408 the display system 134 to present the additional 2D ultrasound image. In various embodiments, the steps 400 may comprise receiving 408 a user input providing a fine angular adjustment to the elevational tilt angle 304. The steps 400 may comprise setting 406 the mechanically wobbling ultrasound probe 104 to an adjusted elevational tilt angle 304 based on the fine angular adjustment. The steps 400 may comprise receiving 408, from the mechanically wobbling ultrasound probe 104, an adjusted two-dimensional (2D) ultrasound image at the adjusted elevational tilt angle 304. The steps 400 may comprise causing 408 the display system 134 to present the adjusted 2D ultrasound image.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically setting an elevational tilt angle of a mechanically wobbling ultrasound probe.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
acquiring, by a mechanically wobbling ultrasound probe of an ultrasound system operating in a volume acquisition mode, an ultrasound volume of a region of interest;
analyzing, by at least one processor of the ultrasound system, the ultrasound volume to identify an ultrasound image slice depicting an anatomical object of interest, the ultrasound image slice corresponding with an elevational tilt angle;
setting, by the at least one processor, the mechanically wobbling ultrasound probe to the elevational tilt angle corresponding with the ultrasound image slice depicting the anatomical object of interest;
acquiring, by the mechanically wobbling ultrasound probe operating in a two-dimensional (2D) ultrasound acquisition mode, a 2D ultrasound image at the elevational tilt angle; and
causing, by the at least one processor, a display system to present the 2D ultrasound image.

2. The method of claim 1, comprising analyzing, by the at least one processor, the 2D ultrasound image to determine whether the anatomical object of interest is accurately depicted based on an amount of movement between the ultrasound image slice and the 2D ultrasound image.

3. The method of claim 2, wherein when the anatomical object of interest is accurately depicted in the 2D ultrasound image based on the amount of movement between the ultrasound image slice and the 2D ultrasound image being below a first image quality threshold:
acquiring, by the mechanically wobbling ultrasound probe operating in the 2D ultrasound acquisition mode, an additional 2D ultrasound image at the elevational tilt angle; and
causing, by the at least one processor, the display system to present the additional 2D ultrasound image.

4. The method of claim 2, wherein when the anatomical object of interest is not accurately depicted in the 2D ultrasound image based on the amount of movement between the ultrasound image slice and the 2D ultrasound image being above a first image quality threshold and below a second image quality threshold:

acquiring, by the mechanically wobbling ultrasound probe operating in the volume acquisition mode, an additional ultrasound volume of a portion of the region of interest in a vicinity of the elevational tilt angle;

analyzing, by the at least one processor, the additional ultrasound volume to identify a new ultrasound image slice depicting the anatomical object of interest, the new ultrasound image slice corresponding with a new elevational tilt angle;

setting, by the at least one processor, the mechanically wobbling ultrasound probe to the new elevational tilt angle corresponding with the new ultrasound image slice depicting the anatomical object of interest;

acquiring, by the mechanically wobbling ultrasound probe operating in the 2D ultrasound acquisition mode, an additional 2D ultrasound image at the new elevational tilt angle; and causing, by the at least one processor, the display system to present the additional 2D ultrasound image.

5. The method of claim 2, wherein when the anatomical object of interest is not accurately depicted in the 2D ultrasound image based on the amount of movement between the ultrasound image slice and the 2D ultrasound image being above a first image quality threshold and above a second image quality threshold:

acquiring, by the mechanically wobbling ultrasound probe operating in the volume acquisition mode, an additional ultrasound volume of the region of interest;

analyzing, by the at least one processor, the additional ultrasound volume to identify a new ultrasound image slice depicting the anatomical object of interest, the new ultrasound image slice corresponding with a new elevational tilt angle;

setting, by the at least one processor, the mechanically wobbling ultrasound probe to the new elevational tilt angle corresponding with the new ultrasound image slice depicting the anatomical object of interest;

acquiring, by the mechanically wobbling ultrasound probe operating in the 2D ultrasound acquisition mode, an additional 2D ultrasound image at the new elevational tilt angle; and causing, by the at least one processor, the display system to present the additional 2D ultrasound image.

6. The method of claim 1, wherein the anatomical object of interest is one or both of:
a particular anatomical structure, or
a particular ultrasound image view of a particular anatomical structure.

7. The method of claim 1, comprising:
receiving, by the at least one processor, a user input providing a fine angular adjustment to the elevational tilt angle;
setting, by the at least one processor, the mechanically wobbling ultrasound probe to an adjusted elevational tilt angle based on the fine angular adjustment;
acquiring, by the mechanically wobbling ultrasound probe operating in the 2D ultrasound acquisition mode, an adjusted two-dimensional (2D) ultrasound image at the adjusted elevational tilt angle; and
causing, by the at least one processor, the display system to present the adjusted 2D ultrasound image.

8. An ultrasound system comprising:
a mechanically wobbling ultrasound probe configured to:
operate in a volume acquisition mode to acquire an ultrasound volume of a region of interest; and
operate in a two-dimensional (2D) ultrasound acquisition mode to acquire a 2D ultrasound image at an elevational tilt angle;
at least one processor configured to:
analyze the ultrasound volume to identify an ultrasound image slice depicting an anatomical object of interest, the ultrasound image slice corresponding with the elevational tilt angle; and
set the mechanically wobbling ultrasound probe to the elevational tilt angle corresponding with the ultrasound image slice depicting the anatomical object of interest; and
a display system configured to present the 2D ultrasound image.

9. The ultrasound system of claim 8, wherein the at least one processor is configured to analyze the 2D ultrasound image to determine whether the anatomical object of interest is accurately depicted based on an amount of movement between the ultrasound image slice and the 2D ultrasound image.

10. The ultrasound system of claim 9, wherein when the anatomical object of interest is accurately depicted in the 2D ultrasound image based on the amount of movement between the ultrasound image slice and the 2D ultrasound image being below a first image quality threshold:
the mechanically wobbling ultrasound probe operating in the 2D ultrasound acquisition mode is configured to acquire an additional 2D ultrasound image at the elevational tilt angle; and
the display system is configured to present the additional 2D ultrasound image.

11. The ultrasound system of claim 9, wherein when the anatomical object of interest is not accurately depicted in the 2D ultrasound image based on the amount of movement between the ultrasound image slice and the 2D ultrasound image being above a first image quality threshold and below a second image quality threshold:
the mechanically wobbling ultrasound probe operating in the volume acquisition mode is configured to acquire an additional ultrasound volume of a portion of the region of interest in a vicinity of the elevational tilt angle;
the at least one processor is configured to:
analyze the additional ultrasound volume to identify a new ultrasound image slice depicting the anatomical object of interest, the new ultrasound image slice corresponding with a new elevational tilt angle; and
set the mechanically wobbling ultrasound probe to the new elevational tilt angle corresponding with the new ultrasound image slice depicting the anatomical object of interest;
the mechanically wobbling ultrasound probe operating in the 2D ultrasound acquisition mode is configured to acquire an additional 2D ultrasound image at the new elevational tilt angle; and
the display system is configured to present the additional 2D ultrasound image.

12. The ultrasound system of claim 9, wherein when the anatomical object of interest is not accurately depicted in the 2D ultrasound image based on the amount of movement between the ultrasound image slice and the 2D ultrasound image being above a first image quality threshold and above a second image quality threshold:
the mechanically wobbling ultrasound probe operating in the volume acquisition mode is configured to acquire an additional ultrasound volume of the region of interest;

the at least one processor is configured to:
  analyze the additional ultrasound volume to identify a new ultrasound image slice depicting the anatomical object of interest, the new ultrasound image slice corresponding with a new elevational tilt angle; and
  set the mechanically wobbling ultrasound probe to the new elevational tilt angle corresponding with the new ultrasound image slice depicting the anatomical object of interest;
the mechanically wobbling ultrasound probe operating in the 2D ultrasound acquisition mode is configured to acquire an additional 2D ultrasound image at the new elevational tilt angle; and
the display system is configured to present the additional 2D ultrasound image.

13. The ultrasound system of claim 8, wherein:
the at least one processor is configured to:
  receive a user input providing a fine angular adjustment to the elevational tilt angle; and
  set the mechanically wobbling ultrasound probe to an adjusted elevational tilt angle based on the fine angular adjustment;
the mechanically wobbling ultrasound probe operating in the 2D ultrasound acquisition mode is configured to acquire an adjusted two-dimensional (2D) ultrasound image at the adjusted elevational tilt angle; and
the display system is configured to present the adjusted 2D ultrasound image.

14. The ultrasound system of claim 13, wherein the mechanically wobbling ultrasound probe comprises a user input device configured to provide the fine angular adjustment of the elevational tilt angle to the at least one processor.

15. A non-transitory computer readable medium having stored thereon, a computer program having at least one code section, the at least one code section being executable by a machine for causing an ultrasound system to perform steps comprising:
  receiving, from a mechanically wobbling ultrasound probe of the ultrasound system operating in a volume acquisition mode, an ultrasound volume of a region of interest;
  analyzing the ultrasound volume to identify an ultrasound image slice depicting an anatomical object of interest, the ultrasound image slice corresponding with an elevational tilt angle;
  setting the mechanically wobbling ultrasound probe to the elevational tilt angle corresponding with the ultrasound image slice depicting the anatomical object of interest;
  receiving, from the mechanically wobbling ultrasound probe operating in a two-dimensional (2D) ultrasound acquisition mode, a 2D ultrasound image at the elevational tilt angle; and
  causing a display system to present the 2D ultrasound image.

16. The non-transitory computer readable medium of claim 15, comprising analyzing the 2D ultrasound image to determine whether the anatomical object of interest is accurately depicted based on an amount of movement between the ultrasound image slice and the 2D ultrasound image.

17. The non-transitory computer readable medium of claim 16, wherein when the anatomical object of interest is accurately depicted in the 2D ultrasound image based on the amount of movement between the ultrasound image slice and the 2D ultrasound image being below a first image quality threshold:
  receiving, from the mechanically wobbling ultrasound probe operating in the 2D ultrasound acquisition mode, an additional 2D ultrasound image at the elevational tilt angle; and
  causing, by the at least one processor, the display system to present the additional 2D ultrasound image.

18. The non-transitory computer readable medium of claim 15, wherein when the anatomical object of interest is not accurately depicted in the 2D ultrasound image based on the amount of movement between the ultrasound image slice and the 2D ultrasound image being above a first image quality threshold and below a second image quality threshold:
  receiving, from the mechanically wobbling ultrasound probe operating in the volume acquisition mode, an additional ultrasound volume of a portion of the region of interest in a vicinity of the elevational tilt angle;
  analyzing the additional ultrasound volume to identify a new ultrasound image slice depicting the anatomical object of interest, the new ultrasound image slice corresponding with a new elevational tilt angle;
  setting the mechanically wobbling ultrasound probe to the new elevational tilt angle corresponding with the new ultrasound image slice depicting the anatomical object of interest;
  receiving, from the mechanically wobbling ultrasound probe operating in the 2D ultrasound acquisition mode, an additional 2D ultrasound image at the new elevational tilt angle; and
  causing the display system to present the additional 2D ultrasound image.

19. The non-transitory computer readable medium of claim 15, wherein when the anatomical object of interest is not accurately depicted in the 2D ultrasound image based on the amount of movement between the ultrasound image slice and the 2D ultrasound image being above a first image quality threshold and above a second image quality threshold:
  receiving, from the mechanically wobbling ultrasound probe operating in the volume acquisition mode, an additional ultrasound volume of the region of interest;
  analyzing the additional ultrasound volume to identify a new ultrasound image slice depicting the anatomical object of interest, the new ultrasound image slice corresponding with a new elevational tilt angle;
  setting the mechanically wobbling ultrasound probe to the new elevational tilt angle corresponding with the new ultrasound image slice depicting the anatomical object of interest;
  receiving, from the mechanically wobbling ultrasound probe operating in the 2D ultrasound acquisition mode, an additional 2D ultrasound image at the new elevational tilt angle; and
  causing the display system to present the additional 2D ultrasound image.

20. The non-transitory computer readable medium of claim 15, comprising:
  receiving a user input providing a fine angular adjustment to the elevational tilt angle;
  setting the mechanically wobbling ultrasound probe to an adjusted elevational tilt angle based on the fine angular adjustment;
  receiving, from the mechanically wobbling ultrasound probe operating in the 2D ultrasound acquisition mode, an adjusted two-dimensional (2D) ultrasound image at the adjusted elevational tilt angle; and causing the display system to present the adjusted 2D ultrasound image.

\* \* \* \* \*